(12) United States Patent
Leushner et al.

(10) Patent No.: US 6,413,718 B1
(45) Date of Patent: *Jul. 2, 2002

(54) METHOD FOR SEQUENCING OF NUCLEIC ACID POLYMERS

(75) Inventors: James Leushner, North York; Jean-Michel Lacroix, Etobicoke; May Hui, Toronto; James M. Dunn, Scarborough, all of (CA); Marina T. Larson, Silverthorne, CO (US)

(73) Assignee: Visible Genetics Inc., Toronto (*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/065,748

(22) Filed: Apr. 24, 1998

Related U.S. Application Data

(63) Continuation-in-part of application No. PCT/US97/07135, filed on Apr. 29, 1997, which is a continuation-in-part of application No. 08/807,138, filed on Feb. 27, 1997, now Pat. No. 5,888,736, which is a continuation-in-part of application No. 08/684,498, filed on Jul. 19, 1996, now Pat. No. 5,830,657, and a continuation of application No. 08/640,672, filed on May 1, 1996, now Pat. No. 5,789,168.

(51) Int. Cl.$^7$ ............................. C12Q 1/68; C12P 19/34
(52) U.S. Cl. .......................................... 435/6; 435/91.2
(58) Field of Search ........................... 435/6, 91.1, 91.2

(56) References Cited

U.S. PATENT DOCUMENTS

| | | | |
|---|---|---|---|
| 4,683,194 A | 7/1987 | Saiki et al. ................. | 435/6 |
| 4,683,195 A | 7/1987 | Mullis et al. ................ | 435/6 |
| 4,683,202 A | 7/1987 | Mullis ........................ | 435/91 |
| 4,729,947 A | 3/1988 | Middendorf et al. ......... | 435/6 |
| 4,795,699 A | 1/1989 | Tabor et al. ................. | 435/5 |
| 4,800,159 A | 1/1989 | Mullis et al. ............. | 435/172.3 |
| 4,811,218 A | 3/1989 | Hunkapiller et al. ... | 364/413.01 |
| 4,889,818 A | 12/1989 | Gelfand et al. ............. | 435/194 |
| 4,942,124 A | 7/1990 | Church ........................ | 435/6 |
| 4,965,188 A | 10/1990 | Mullis et al. ............... | 435/6 |
| 5,008,182 A | 4/1991 | Sninsky et al. ............. | 435/5 |
| 5,075,216 A | 12/1991 | Innis et al. ................. | 435/6 |
| 5,079,352 A | 1/1992 | Gelfand et al. .............. | 538/27 |
| 5,122,345 A | 6/1992 | Tabor et al. ................. | 422/116 |
| 5,124,247 A | 6/1992 | Ansorge ....................... | 435/6 |
| 5,171,534 A | 12/1992 | Smith et al. ............. | 422/82.05 |
| 5,175,082 A | 12/1992 | Jeffreys ...................... | 435/6 |
| 5,176,995 A | 1/1993 | Sninsky et al. ............. | 435/6 |
| 5,207,880 A | 5/1993 | Middendorf et al. ..... | 204/182.8 |
| 5,283,171 A | 2/1994 | Manos et al. ............... | 435/5 |
| 5,352,600 A | 10/1994 | Gelfand et al. ............. | 435/194 |
| 5,418,149 A | 5/1995 | Gelfand et al. | |
| 5,427,911 A | 6/1995 | Ruano ......................... | 435/6 |
| 5,453,355 A | 9/1995 | Birkenmeyer et al. ..... | 435/6 |
| 5,484,701 A | 1/1996 | Cocuzza et al. ............. | 435/6 |
| 5,527,898 A | 6/1996 | Bauer et al. ............... | 536/24.3 |

FOREIGN PATENT DOCUMENTS

| | | |
|---|---|---|
| EP | 0265293 | 4/1988 |
| EP | 0386859 | 9/1990 |
| EP | 0655506 | 5/1995 |
| WO | 8907149 | 8/1989 |
| WO | 9218650 | 10/1992 |
| WO | 9302212 | 2/1993 |
| WO | 9308305 | 4/1993 |
| WO | 9426894 | 11/1994 |
| WO | 9504140 | 2/1995 |
| WO | 9506756 | 3/1995 |
| WO | 9511961 | 5/1995 |
| WO | 9601008 | 1/1996 |
| WO | 9601909 | 1/1996 |
| WO | WO 98/24930 | 6/1998 |

OTHER PUBLICATIONS

Andersson et al. Analy.Biochem. 218:300–318, 1994.*
Weiss et a. Biochemistry 22(19):4501–4507, 1983.*
Wiemann et al. Analy.Biochem 224:117–121, 1995.*
Tabor et al., "A single residue in DNA Polymerases of the *Escherichia coli* DNA polymerase I family is critical for distinguishing between deoxy and dideoxynucleotides", *Proc. Nat'l Acad. Sci. USA.*92: 6339–6343 (1995).
Reeve et al., A novel thermostable polymerase for DNA sequencing *Nature* 376: 796–797 (1995).
Sarkar et al., "Dideoxy Fingerprinting (ddF): A rapid and Efficient Screen for the Presence of Mutations" *Genomics* 13: 441–443 (1992).
Wiemann et al., "Simultaneous On–Line Sequencinbg on Both Strands with Two Fluorescent Dyes" *Anal. Biochem.* 224: 117–121 (1995).
Murakawa et al., :Direct Detection of HIV–1 RNA from AIDS and ARC Patient Samples *DNA* 7: 287–295 (1988).
Carothers et al., "Point Mutation Analysis in A Mammalian Gene: Rapid Preparation of Total RNA, PCR Amplification of cDNA, and Taq Sequencing by a Novel Method" *BioTechniques* 7: 494–498 (19.

(List continued on next page.)

Primary Examiner—Eggerton A. Campbell
(74) Attorney, Agent, or Firm—Oppedahl & Larson LLP (57) ABSTRACT

Sequencing of a selected region of a target nucleic acid polymer in a natural abundance DNA sample can be performed in a single vessel by combining the sample with a sequencing mixture containing a primer pair, a thermally stable polymerase such as Thermo Sequenase™ which incorporates dideoxynucleotides into an extending nucleic acid polymer at a rate which is no less than about 0.4 times the rate of incorporation of deoxynucleotides, nucleotide feedstocks, and a chain terminating nucleotide. The reaction mixture also includes an unconventional nucleotide and an appropriate enzyme for degradation of nucleic acid polymers containing the unconventional nucleotide. The mixture is processed through multiple thermal cycles for annealing, extension and denaturation to produce a product mixture which is analyzed by electrophoresis.

15 Claims, 6 Drawing Sheets

OTHER PUBLICATIONS

Murray, V., "Improved Double–Stranded DNA Sequencing Using the Linear Polymerase Chain Reaction", *Nucl. Acids Res.* 17: 8889 (1989).

Mahony et al., "Multiplex PCR for Detection of Chlamydia trachomatis and Neisseria gonorhoeae in Genetourinary specimens" *J. Clin. Microbiol.* 33: 3049–3053 (1995).

Kaltenboeck et al, "Two–Step Polymerase Chain Reaction and Restriction Endonuclease Analyses Detect and Differentiate ompA DNA of Chlmaydia spp." *J. Clin. Microbiol.* 30: 1098–1104 (1992).

Mahony et al., "Confirmatory Polymerase Chain Reaction Testing for Chlamydia trachomatis in First–Void Urine from Asymptomatic and Symptomatic Men" *J. Clin. Microbiol.* 30: 2241–2245 (1992).

Ruano et al., "Coupled Amplification and sequencing of geneomic DNA", *Proc. Nat'l Acad. Sci (USA)* 88: 2815–2819 (1991).

Ewanowitch et al., "Major Outbreak of Pertussis in Northern Alberta Canada: Analysis of Discrepant Direct Fluorescent–Antibody Culture Results by Using Polymerase Chain Reaction Methodology" *J. Clin. Microbiol.* 31: 1715–1725 (1993).

Erickson, D., "Diagnosis by DNA", *Scientific American*, p. 116 (1992).

Eisenstein, B., "The Polymerase Chain Reaction", *New Engl. J., Med.* 332: 178–183 (1990).

De Schryver et al., "Epidemiology of sexually transmitted diseases: the global picture", *Bull. WHO* 68: 639–654 (1990).

Church et al., "The Genomic Sequencing Technique", *Medical Genetics: Past, Present, Future* pp. 17–21 (1985).

Church et al., "Genomic Sequencing", *Proc. Nat'l Acad. Sci. (USA)* 81: 1991–1995 (1984).

Bej et al., "Multiplex PCR amplification and immobilized caputre probes for detection of bacterial pathogens and indicators in water" *Molec. Cellular Probes* 4: 353–365 (1990).

Bej et al., "Detection of Coliform Bacteria and Escherichia coli by Multiplex Chain Reaction: Comparison with Defined Substrate and Plating Methods for Water Quality Monitoring" *Appl. Environ. Microbiol.* 57: 2429–2432 (1991).

Beebe et al., "Incidence of Neisseria gonorrhoeae Isolates Negative by Syva DDirect Fluorescent–Antibody Test but Positve by Gen–Prove Accuprobe Test in a Sexually Transmitted Disease Clinic Population" *J. Clim. Microbiol.* 31: 2535–2537 (1993).

Way et al., "Specific Detection of Salmonella spp. by Multiplex Polymerase Chain Reaction" *Appl. Environ. Microbiol.* 59: 1473–1479 (1993).

Warren et al., "Comparative Evaluation of Detection Assays for Chlamydia trachomatis" *J. Clin. Microbiol.* 31: 1663–1666 (1993).

Thermosequenase Product Insert (1995).

Maxam et al., "A new method for sequencing DNA", *Proc. Nat'l. Acad. Sci. (USA)* 74: 560–564 (1977).

Smith et al., "Fluorescence Detection in automated DNA Sequence analysis" *Nature* 321: 674–679 (1986).

Langemeier et al., "Application of Cycle Dideoxy Fingerprinting to Screening Heterogeneous Polpulations of the Equine Infectious Anemia Virus", *Biotechniques* 17 (1994).

Ruano et al., Automated Genomic Coupled Amplification and Sequencing (CAS) of the Mitochondrial D Loop, Genomic Analysis Conference, Hilton Head, Fall 1994.

Arnot et al. "Digital codes from hypervariable tandemly repeated DNA sequences in the Plasmodium falciparum circumsporozoite gene can genetically barcode isolates" *Molec. Biochem. Parasitol.* 61: 15–24 (1993).

Ellison et al., "Detection of Mutations and Polymorphisms Using Fluorescence–Based Dideoxy Fingerprinting (F–ddF)", *Biotechniques* 17: 742–753 (1994).

Sanger et al., "DNA sequencing with chain–terminating inhibitors" *Proc. Nat'l. Acad. Sci.* 74: 5463–5467 (1977).

Rao, V. B.,"Direct–Sequencing of Polymerase Chain Reaction–Amplified DNA", *Anal Biochem*, 216: 1–14 (1994).

Kretz et al., "Cycle Sequencing" in *PCR Methods and Applications* 3: S107–S112 (1994).

Deng et al., "Simultaneous amplification and sequencing of genomic DNA (SAS): sequencing of 16S rRNA genes using total genomic DNA from *Butyrovibrio fibrisolvens*, and detection and genotyping of non–cultruable mycoplasma–like organisms directly from total DNA isolated from infected plants", *J. Microbiol. Methods* 17: 103–113 (1993).

Innis et al., *Proc. Natl. Acad. Sci. USA* 85:9436–9440 (Dec. 1988).

Mason, *BioTechniques* 12:60–62 (Jan. 1992).

Reynolds et al., *BioTechniques* 15:462–467 (Mar. 1993).

Xu et al. *Mutation Res.* 288:237–248 (1993).

Nuovo, G.J., "In situ PCR" in Dieffenback et al., *PCR Primer: A Laboratory Manual*, pp. 235–248, Cold Spring Harbor Laboratory Press (1995).

Kambara et al, "Real Time Automated Simultaneous Doule Stranded DNA Sequencing Using Two–Color Fluorophore Labeling" *Biotechnology* 9: 648–651 (1991).

Gyllenstein et al., "Generation of single–stranded DNA by polymerase chain reaction and its application to direct sequencing of the HLA–DQA locus" *Proc. Nat'l Acad. Sci. USA* 85: 7652–7656 (1988).

Mullis et al., "Specific Synthesis of DNA in Vitro via a Polymerase–Catalyzed Chain Reaction" *Meth. Enzymol.* 155: 335–350 (1987).

Ruano et al., "Genotyping and haplotyping of polymorphisms directly from genomic DNA via coupled amplification and sequencing (CAS)" *Nucl. Acids Res.* 19: 6877–6882 (1991).

Miller et al., "Chain Terminator Sequencing of Double–Stranded DNA With Built in Error Correction", General Atomics Pre–Print (1991).

\* cited by examiner

METHOD FOR SEQUENCING OF NUCLEIC ACID POLYMERS

This application is a continuation-in-part of International Patent Application No. PCT/US97/07135 filed Apr. 29, 1997, designating the United States, which is a continuation-in-part of U.S. patent application Ser. No. 08/640,672 filed May 1, 1996, U.S. Pat. No. 5,789,168, Ser. No. 08/684,498 filed Jul. 19, 1996 U.S. Pat. No. 5,830,657 and Ser. No. 08/807,138 filed Feb. 27, 1997 U.S. Pat. No. 5,888,736. All of these applications are incorporated herein by reference.

BACKGROUND OF THE INVENTION

This application relates to DNA sequencing reactions, and in particular to improved sequencing reaction protocols making use of thermally stable polymerase enzymes having reduced error rates.

DNA sequencing can be performed in two distinct environments: a research environment in which each procedure is fairly unique and in which the sequence being determined is generally not known prior to completion of the sequence determination; and a diagnostic environment in which the same procedure is repeated on many samples and the sequences being determined are generally known. While the basic procedures used in these two environments can be the same, requirements for speed, cost-effectiveness and low risk of error in the diagnostic environment make many of the techniques actually employed too cumbersome to permit their effective utilization. This has limited the availability of sequencing-based diagnostics, and has indeed led some to question whether sequencing can ever be cost effective for routine diagnostic use.

The ideal DNA sequencing procedure for use in a diagnostic environment would have the following characteristics: (1) it would be able to utilize a DNA-containing sample which had been subjected to only minimal pretreatment to make the DNA accessible for sequencing; (2) it would require combining this sample with only a single reaction mixture, thus reducing risk of error and contamination, and increasing the ease with which the procedure can be automated; and (3) it would require a short amount of time to perform the sequence determination, thus decreasing the marginal costs in terms of equipment and labor for performing the test.

DNA sequencing, whether for research or diagnostics, is generally performed using techniques based on the "chain termination" method described by Sanger et al., *Proc. Nat'l Acad. Sci. (USA)* 74(12):5463–5467 (1977). Basically, in this process, DNA to be tested is isolated, rendered single stranded, and placed into four vessels. In each vessel are the necessary components to replicate the DNA strand, i.e., a template-dependant DNA polymerase, a short primer molecule complementary to a known region of the DNA to be sequenced, and the standard deoxynucleotide triphosphates (dNTP's) commonly represented by A, C, G and T, in a buffer conducive to hybridization between the primer and the DNA to be sequenced and chain extension of the hybridized primer. In addition, each vessel contains a small quantity of one type (i.e., one species) of dideoxynucleotide triphosphate (ddNTP), e.g. dideoxyadenosine triphosphate (ddA).

In each vessel, the primer hybridizes to a specific site on the isolated DNA. The primers are then extended, one base at a time to form a new nucleic acid polymer complementary to the isolated pieces of DNA. When a dideoxynucleotide triphosphate is incorporated into the extending polymer, this terminates the polymer strand and prevents it from being further extended. Accordingly, in each vessel, a set of extended polymers of specific lengths are formed which are indicative of the positions of the nucleotide corresponding to the dideoxynucleotide in that vessel. These sets of polymers are then evaluated using gel electrophoresis to determine the sequence.

As Church and Gilbert observed, "in a mammalian cell, the DNA corresponding to any gene sequence is surrounded by DNA corresponding to some million other sequences." "The Genomic Sequencing Technique" in *Medical Genetics: Past, Present and Future*, Alan R. Liss, Inc., pp. 17–21, (1991). The same is true, to a greater or lesser extent, of any complex DNA sample, e.g. containing microbial genetic materials, plant genetic materials, complete cDNA libraries etc. In the past, DNA sequencing procedures have dealt with this complexity by adding steps which substantially purify the DNA of interest relative to other DNA species present in the sample. This purification has been accomplished by cloning of the DNA to be sequenced prior to sequencing, or by amplification of a selected portion of the genetic material in a sample to enrich the concentration of a region of interest relative to other DNA. For example, it is possible to amplify a selected portion of a gene using a polymerase chain reaction (PCR) as described in U.S. Pat. Nos. 4,683,194, 4,683,195 and 4,683,202, which are incorporated herein by reference. This process involves the use of pairs of primers, one for each strand of the duplex DNA, that will hybridize at a site located near a region of interest in a gene. Chain extension polymerization (without a chain terminating nucleotide) is then carried out in repetitive cycles to increase the number of copies of the region of interest many times. The amplified polynucleotides are then separated from the reaction mixture and used as the starting sample for the sequencing reaction. Gelfand et al. have described a thermostable enzyme, "Taq polymerase," derived from the organism *Thermus aquaticus*, which is useful in this amplification process. (See U.S. Pat. Nos. 4,889,818; 5,352,600 and 5,079,352 which are incorporated herein by reference) Taq polymerase has also been disclosed as useful in sequencing DNA when certain special conditions are met. U.S. Pat. No. 5,075,216, incorporated herein by reference.

Improvements to the original technique described by Sanger et al. have included improvements to the enzyme used to extend the primer chain. For example, Tabor et al. have described enzymes such as T7 DNA polymerase which have increased processivity, and increased levels of incorporation of dideoxynucleotides. (See U.S. Pat. No. 4,795,699 and EP-A-0 386 857, which are incorporated herein by reference). More recently, Reeve et al. have described a thermostable enzyme preparation, called Thermo Sequenase™, with improved qualities for DNA sequencing. *Nature* 376: 796–797 (1995); EP-A-0 655 506, which is incorporated herein by reference. For sequencing, the Thermo Sequenase™ product is used with an amplified DNA sample containing 0.5–2 µg of single stranded DNA (or 0.5 to 5 µg of double stranded DNA) into four aliquots, and combining each aliquot with the Thermo Sequenase™ enzyme preparation, one dideoxynucleotide termination mixture containing one ddNTP and all four dNTP's; and one dye-labeled primer which will hybridize to the DNA to be sequenced. The mixture is placed in a thermocycler and run for 20–30 cycles of annealing, extension and denaturation to produce measurable amounts of dye-labeled extension products of varying lengths which are then evaluated by gel electrophoresis. EP-A-0 655 506 further asserts that Thermo Sequenase™ and similar enzymes can be used for amplification reactions.

Notwithstanding the observations in the art that enzymes useful for amplification can also be used for sequencing, and vice versa, efforts to combine the amplification reaction and the sequencing reaction into a single step have been limited. Ruano and Kidd, *Proc. Nat'L Acad. Sci. (USA)* 88: 2815–2819 (1991) and U.S. Pat. No. 5,427,911, which are incorporated herein by reference, describe a process which they call "coupled amplification and sequencing" (CAS) for sequencing of DNA. In this process, a sample is treated in a first reaction stage with two primers and amplified for a number of cycles to achieve 10,000 to 100,000-fold amplification. A ddNTP is then added during the exponential phase of the amplification reaction, and the reaction is processed for additional thermal cycles to produce chain-terminated sequencing fragments. The CAS process does not achieve the criteria set forth above for an ideal diagnostic assay because it requires an intermediate addition of reagents (the ddNTP reagents). This introduces and opportunity for error or contamination and increases the complexity of any apparatus which would be used for automation.

The problem of errors occurring during amplification has been addressed in one approach through the incorporation into the extending polymers of unusual nucleotides (for example dUTP) which are subject to enzymatic attack (for example with uracil-N-glycosylase) and degradation. See U.S. Pat. No. 5,418,149, which is incorporated herein by reference. Such molecules can be in utilized in most of the same ways that conventional amplification are used, but can be eliminated as contaminants from other reactions by incorporation of a pre-treatment step utilizing an appropriate enzyme to degrade the modified nucleic acid polymers.

It is an object of the present invention to provide a method for sequencing of high-complexity DNA samples which is well-suited for use in the diagnostic environment and for automation and which provides a means for minimizing errors caused by contamination and nucleic acid polymer carryover.

It is a further object of the invention to provide a method for sequencing of DNA which utilizes a DNA-containing sample which had been subjected to only minimal pretreatment to make the DNA accessible for sequencing and which provides a means for minimizing errors caused by contamination and nucleic acid polymer carryover.

It is still a further object of the invention to provide a method for sequencing of DNA which requires combining a complex DNA-containing sample with only a single reaction mixture, thus reducing risk of error and contamination, and increasing the ease with which the procedure can be automated.

SUMMARY OF THE INVENTION

The present invention provides a method for sequencing a region of interest in a DNA sample in which a single set of reagents is added to a minimally-treated sample to produce useful sequencing results. The invention is based on the surprising observation and discovery that the addition of a reaction mixture containing the thermostable polymerase Thermo Sequenase™, two primers which bind to complementary strands of a target DNA molecule at sites flanking the region of interest, a mixture of nucleotide triphosphates (A, C, G and T) and one dideoxynucleotide triphosphate to a DNA sample which contains target and non-target DNA in substantially natural abundance, including highly complex DNA samples such as genomic human DNA, and the processing of the combination through multiple cycles of annealing, extension and denaturation results in the production of a mixture which can be loaded directly onto a gel for sequence analysis of the region of interest. The reaction mixture also includes an unconventional nucleotide and an appropriate enzyme for degradation of nucleic acid polymers containing the unconventional nucleotide.

One aspect of the present invention is a method for sequencing a selected region of a target nucleic acid polymer comprising the steps of (a) combining a natural abundance sample containing the target nucleic acid polymer with a reaction mixture comprising three types of deoxynucleotide triphosphates, an unconventional nucleotide triphosphate corresponding to the fourth type of base, a dideoxynucleotide triphosphate, first and second primers, an enzyme which degrades nucleic acid polymers incorporating the unconventional nucleotide, and a thermally stable polymerase enzyme which incorporates dideoxynucleotides into an extending nucleic acid polymer at a rate which is no less than about 0.4 times the rate of incorporation of deoxynucleotides to form a reaction mixture, said first and second primers binding to the sense and antisense strands, respectively, of the target nucleic acid polymer at locations flanking the selected region;

(b) exposing the reaction mixture to an initial stage in which the enzyme that degrades nucleic acid polymers incorporating the unconventional nucleotide is active for a period of time sufficient to degrade nucleic acid polymers containing the unconventional nucleic acid which may be present in the sample;

(c) exposing the reaction mixture to a plurality of temperature cycles each of which includes at least a high temperature denaturation phase and a lower temperature extension phase to produce a product mixture comprising sequencing fragments which are terminated by incorporation of the dideoxynucleotide; and (d) evaluating the product mixture to determine the lengths of the sequencing fragments produced.

DETAILED DESCRIPTION OF THE INVENTION

The present invention answers the need for a simple and readily-automated sequencing procedure which can be used directly on samples which contain complex mixtures of DNA. To distinguish such mixtures from DNA preparations which have been sequenced in the past, the specification and claims of this application use the term "natural abundance sample" to describe such a mixture. As used herein a "natural abundance sample" is a sample which has been treated to make DNA in the sample accessible for hybridization with oligonucleotide primers, for example by lysis, centrifugation to remove cellular debris and proteolytic digestion to expose the DNA, but which has not been subjected to a preferential purification or amplification step to increase the amount of target DNA relative to non-target DNA present in the initial sample. The term "natural abundance" does not, however, require the presence of all the DNA from the original sample. Thus, a complex sample containing just nuclear DNA, or just mitochondrial DNA or some subfraction of nuclear or mitochondrial DNA obtained by isolation from a tissue sample but not subjected to preferential amplification would be a "natural abundance" sample within the meaning of that term in the specification and claims of this application. The term "natural abundance" would also include a DNA sample prepared by conversion, for example by reverse transcription, of a total mRNA preparation or the genome of an RNA virus to cDNA; DNA isolated from an individual bacterial colony growing on a plate or from an enriched bacterial culture; and a viral DNA preparation where substantially the entire viral genome is isolated. The term "natural abundance" does not encompass a sample in which the isolated DNA is not a complex combination of DNA molecules, and thus would not encompass, for example, a purified plasmid preparation containing only a single species of plasmid.

Natural abundance samples of mammalian DNA can be prepared from fluid samples, e.g., blood or urine or tissue samples by any of a number of techniques, including lysis, centrifugation to remove cellular debris and proteolytic digestion to expose the DNA; salt precipitation or standard SDS-proteinase K-phenol extraction. Natural abundance samples can also be prepared using kits, for example the Gentra Pure Gene DNA Isolation Kit.

The method of the invention utilizes the properties of enzymes like Thermo Sequenase™, namely the ability to incorporate dideoxynucleotides into an extending polynucleotide at a rate which is no less than about 0.4 times the rate of incorporation of deoxynucleotides, to provide a method for the sequencing of a nucleic acid polymer from a natural abundance sample in a single set of thermocycling reactions which can be carried out in a single vessel. Thus, the method of the invention is ideally suited for automation.

Figure 1:
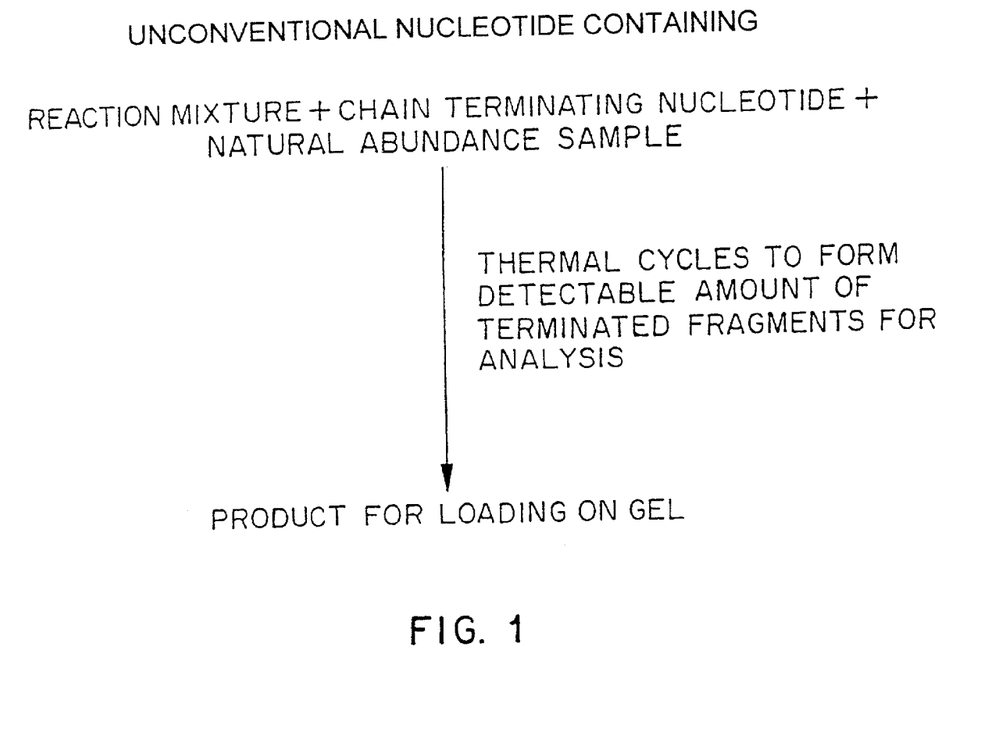
FIG. 1 illustrates the method of the invention schematically.

FIG. 1 illustrates the fundamental simplicity and elegance of the method of the invention in flow chart form. As shown in FIG. 1, a sample containing a target nucleic acid polymer which includes a region to be sequenced is combined with a reaction mixture containing two primers, a mixture of dNTP's, a chain terminating nucleotide triphosphate, i.e., a dideoxynucleotide triphosphate, and a thermostable polymerase with a high affinity for ddNTP incorporation in a buffer suitable for hybridization and template-dependant polymerization. The mixture is processed for a number of thermal cycles sufficient to produce detectable amounts of sequencing fragments, generally from 20 to 50 cycles. During each cycle, the primers each anneal to the respective strand of target DNA present in the sample, and primer chain extension using the polymerase enzymes and the nucleotide triphosphate feedstocks proceeds until terminated by incorporation of a chain-terminating nucleotide triphosphate. This results in the production of sequencing fragments comparable to those generated in a conventional sequencing reaction. Analysis of these fragments provides information concerning the sequence of the selected region of the target DNA. Those extension products which are not terminated prior to reaching the region complementary to the other primer can serve as template for generation of sequencing fragments in later cycles, although this generally occurs to a very small extent. Finally, the product mixture containing dideoxy-terminated fragments is loaded onto an electrophoresis gel for analysis of the positions of the base corresponding to the chain-terminating nucleotide triphosphate with in the target nucleic acid polymer.

The operation of the invention can be understood in the context of a hypothetical 200 nt DNA fragment having equal amounts of each base. This means that there will be 50 potential truncation events during the cycle. For each cycle, some of the products would be full length (and thus able to hybridize with one of the two primers to produce more sequencing fragments) and some would be truncated at the points where the ddNTP was added. If each of these truncation events has a statistical likelihood of occurring 1 time in 500 as a result of the relative concentration of ddNTP compared to dNTP and the relative incorporation by the enzyme, then overall a truncation product will occur in slightly less than ten percent of the reactions. Table 1 shows the relative amounts of full-length and chain-termination products theoretically formed after 10, 20 and 30 cycles of a reaction according to the invention using this 200 nt polynucleotide assuming various ratios of truncated to full-length product.

TABLE 1

| Cycles | truncation ratio = 0.1 | | truncation ratio = 0.3 | | truncation ratio = 0.5 | |
| --- | --- | --- | --- | --- | --- | --- |
| | truncated | full-length | truncated | full-length | truncated | full-length |
| 10 | 32 | 613 | 86 | 202 | 57 | 57 |
| 20 | 41,000 | 376,000 | 17,400 | 40,462 | 3,300 | 3,300 |
| 30 | 25.6 × 10$^6$ | 230 × 10$^6$ | 3.5 × 10$^6$ | 8.2 × 10$^6$ | 190,000 | 190,000 |

The absolute and relative amounts of nucleotide triphosphates and chain-terminating nucleotide triphosphates may be optimized for the particular enzyme employed. In actual practice, it has been found that useful results are obtained with Thermo Sequenase™ when the reaction is run for 35 to 45 cycles, using a dideoxy:deoxy mole ratio of 1:100 to 1:300. In general, each nucleotide triphosphate will be included in the reaction mixture at concentrations of from 250 $\mu$M to 1.5 mM, and the chain-terminating nucleotide triphosphate will be included at a level of from 0.5 $\mu$M to 30 $\mu$M to produce compositions in which the mole ratio of the chain terminating nucleotide triphosphate to the corresponding nucleotide triphosphate is from 1:50 to 1:1000, preferably from 1:100 to 1:500. This will result in incorporation of a chain-terminating nucleotide triphosphate into from 30 to almost 100 percent of the extending polymer chains formed during the thermal cycling of the reaction mixture.

A key factor in successfully performing the method of the invention is the utilization of Thermo Sequenase™ or a comparable enzyme as the thermostable polymerase in the reaction mixture. Such enzymes are characterized by a high affinity for incorporating dideoxynucleotides into the extending nucleotide chain. In general, for purposes of the present invention, the polymerase used should be one which incorporates dideoxynucleotides into an extending nucleic acid polymer at a rate which is no less than about 0.4 times the rate of incorporation of deoxynucleotides. Thermo Sequenase™ is known to favor the incorporation of dideoxynucleotides, and is suitable for use in the invention.. Tabor et al. have also described enzymes having increased processivity and high and increased levels of incorporation of dideoxynucleotides. (See EP 0 655 506). Roche sells a polymerase under the trademark TAQ-FS which meets these criteria as well.

Figure 2A:
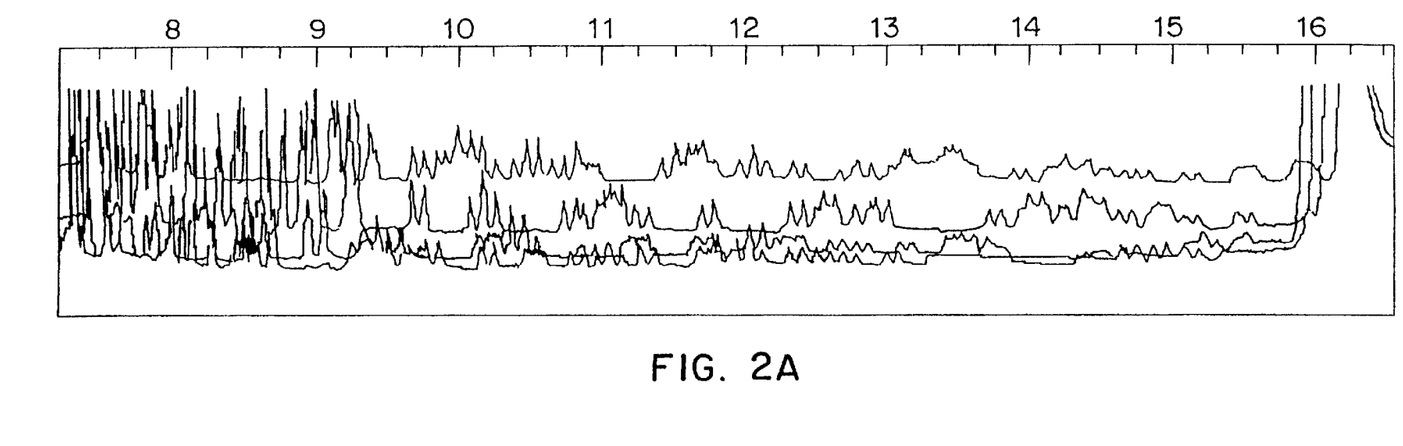
FIGS. 2A and 2B show a comparison of sequencing runs performed using Thermo Sequenase™ as the polymerase in the method of the invention with results obtained using other thermostable polymerases in a comparative experiment.
Figure 2B:
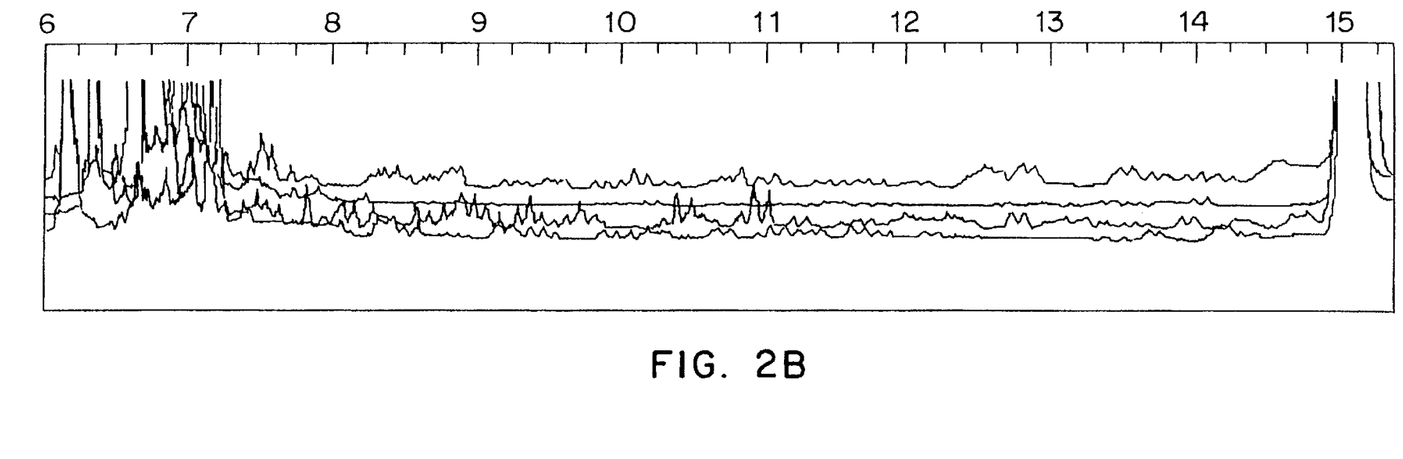
Figure 3:
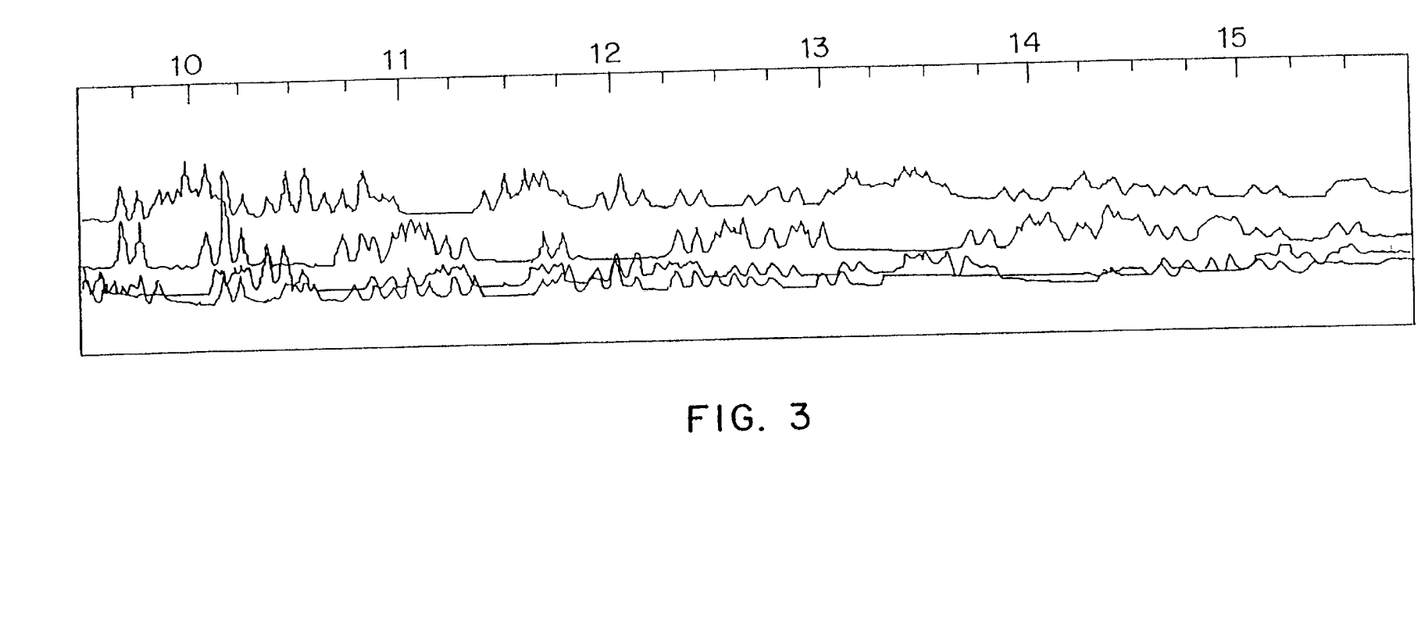
FIG. 3 shows the data trace of FIG. 2A in greater detail.

FIGS. 2A and 2B and FIG. 3 illustrate the importance of this characteristic of the polymerase enzyme employed. FIGS. 2A and 3 shows a sequencing data trace for an actual heterozygous patient sample of natural abundance DNA which was obtained using Thermo Sequenase™ and primers flanking exon 2 of the Von Hippel-Lindau gene in a process according to the invention. Large, well-defined peaks corresponding to the termination fragments were obtained which made sequence evaluation of the sample very straightforward. In addition, the peaks for homozygous peaks are all approximately the same size, and are readily distinguishable from peaks for bases at heterozygous locations. This result was obtained performing the test in a single reaction vessel, with a single unaugmented reaction mixture, in a total of 45 thermal cycles. Comparable results could be obtained using fewer reaction cycles, for example 35 cycles as shown in Example 1 herein.

In contrast, FIG. 2B shows the trace obtained when a combination of Vent and Sequitherm™ were used instead of Thermo Sequenase™ for a total of 45 thermal cycles. In this trace, the peaks for the termination fragments are much smaller and less well defined. Furthermore, the peaks are quite variable in height and did not permit identification of heterozygous peaks based on peak height. Performing the same experiment using Taq polymerase alone resulted in a data trace that contained no usable peaks.

In the method of the invention, a natural abundance sample containing, or suspected to contain, a target DNA sequence is combined in a reaction mixture with an appropriate polymerase, all four types of deoxynucleotide triphosphates, a dideoxynucleotide triphosphate, and first and second primers. The primers used in the method of the present invention can be any pair of primers which hybridize with the sense and antisense strands of the target DNA flanking a selected region that is to be sequenced, and which do not both hybridize to neighboring locations in human DNA or other DNA potentially found in the sample. As used herein, the term "flanking" will be understood to mean the positioning of primers at the 5'-ends of the selected region on each DNA strand, such that extension of the primers leads to replication of the region between the primers. The primers are preferably selected such that the primer pair flanks a region that is about 500 bp or less, although primers spanning larger regions of DNA can be utilized with adjustments to the sequencing mixture (generally an increase in the relative amount of deoxynucleotide triphosphates) to increase the amount of longer sequencing fragments produced.

Primers can be selected to hybridize with highly conserved regions which are the same in all variants of the target DNA or can be prepared as degenerate primers to take known sequence variations at the primer site into account. Thus, the first and second primers of the invention may each be a discrete oligonucleotide species, or may be a set of oligonucleotide primers with similar but not identical sequences.

One or both of the primers may be labeled with a detectable label at the 5'-end thereof, particularly a fluorescent label such as fluorescein or a cyanine dye such as Cy 5.5. If labels are used on both primers, the labels selected should be spectroscopically-distinct, i.e., they should have either a different excitation spectrum or a different emission spectrum such that one primer can be distinguished from the other. When both primers are labeled with different detectable labels, for example with two different fluorophores as in the process described by Wiemann et al., "Simultaneous On-Line DNA Sequencing on Both Stands with Two Fluorescent Dyes," *Anal. Biochem* 224: 117–121 (1995), the sequence of both strands of the sample can be determined in a single reaction.

The nucleotide triphosphate feedstock mixture is a standard mixture of three of the four conventional deoxynucleotide bases (A, C, G and T), plus an unconventional nucleotide corresponding to the fourth base in a buffer suitable for template-dependent primer extension with the enzyme employed. As will be appreciated by persons skilled in the art, the specific concentrations of the nucleotide triphosphates and the nature of the buffer will vary depending on the enzyme employed. Standard buffers and reagent concentrations for various known polymerase enzymes may be employed in the invention.

The term "unconventional nucleotides" refers to unnatural or analog type nucleotide triphosphates that can be polymerized in a template dependent manner into the sequencing fragments. Unnatural forms of modified nucleotides include alkylated nucleotides and nucleotides modified by alkylhydroxylation. Specific examples of modified nucleotides includes but are not limited to N-7 methylguanine, deoxyuridine, deoxyinosine, deoxy-5,6-dihydroxythymine (from $OsO_4$,treated DNA), 5',6'-dihydroxydihydrothymine, and deoxy-3'-methyladenosine. Unconventional nucleotides may also include natural forms of nucleotides which are not conventionally incorporated in DNA. Thus, for purposes of the present invention, uracil and hypoxanthine are unconventional nucleotides.

An important characteristic of the unconventional nucleotides used in the invention is existence of an enzyme which will degrade polynucleotides containing the unconventional nucleotides to make them unsuitable as substrates for further generatio of sequencing fragments at temperatures below those normally associated with generation of sequencing fragments using a thermostable polymerase. The reaction mixture in accordance with the invention includes an appropriate enzyme, frequently a glycosylase. Examples of specific enzymes include: uracil N-glycosylase, hypoxanthine-DNA glycosylase, 3-methyladenine-DNA glycosylase I and II, hydroxymethyl uracil-DNA glycosylase and foramidopyrimidine DNA glycosylases. The enzyme is preferably a thermolabile enzyme so that it is active for destruction of carry-over polynucleotides prior to the first sequencing reaction, but inactive thereafter. Care should be taken in the selection of reaction conditions so that the temperature is not lowered after synthesis of sequencing fragments to a temperature which will permit significant degradation of the desired products prior to analysis.

The reaction mixture used in the present invention also includes at least one type (or one species) of chain-terminating nucleotide triphosphate. Separate reactions for the four different types of bases may be run either concurrently or successively. Running all four bases concurrently comports with conventional sequencing practice. However, a preferred embodiment of the present invention combines the single vessel methodology of this application with "single track sequencing" which is described in commonly assigned U.S. patent application Ser. No. 08/577,858 U.S. Pat. No. 5,834,189. In single track sequencing, the determination of the positions of only one (or in any event less than 4) nucleotide(s) of a target sequence is frequently sufficient to establish the presence of and determine the qualitative nature of a target microorganism by providing a finger-print or bar-code of the target sequence that may be sufficient to distinguish it from all other known varieties of the sequence. Throughput is increased by reducing the number of reactions and electrophoresis runs required to identify a sequence. By selection of the order of bases tested, and intermediate analysis, it may be unnecessary to run all four bases to determine the presence and specific qualitative nature of any target microorganism present in the sample.

The present method can be used in combination with any type of detection system that is compatible with the label employed on the primers. For example, a Pharmacia A.L.F. sequencer may be employed when fluorescein-labeled primers are used, while a Visible Genetics MicroGene Blaster is appropriate when the label used is Cy5.5. When multiple labels are used, the sample can be processed on multiple instruments, or it can be evaluated on an instrument which is capable of detecting signals from multiple labels. An example of such an instrument is the Prism 377 Sequencer (Applied Biosystems Inc.) which detects and distinguishes between 4 dyes in a single lane. Spectroscopically distinguishable dyes which are recognized by the Prism 377 are the FAM, ROX, TAMRA and JOE dyes known in the art.

Figure 4:
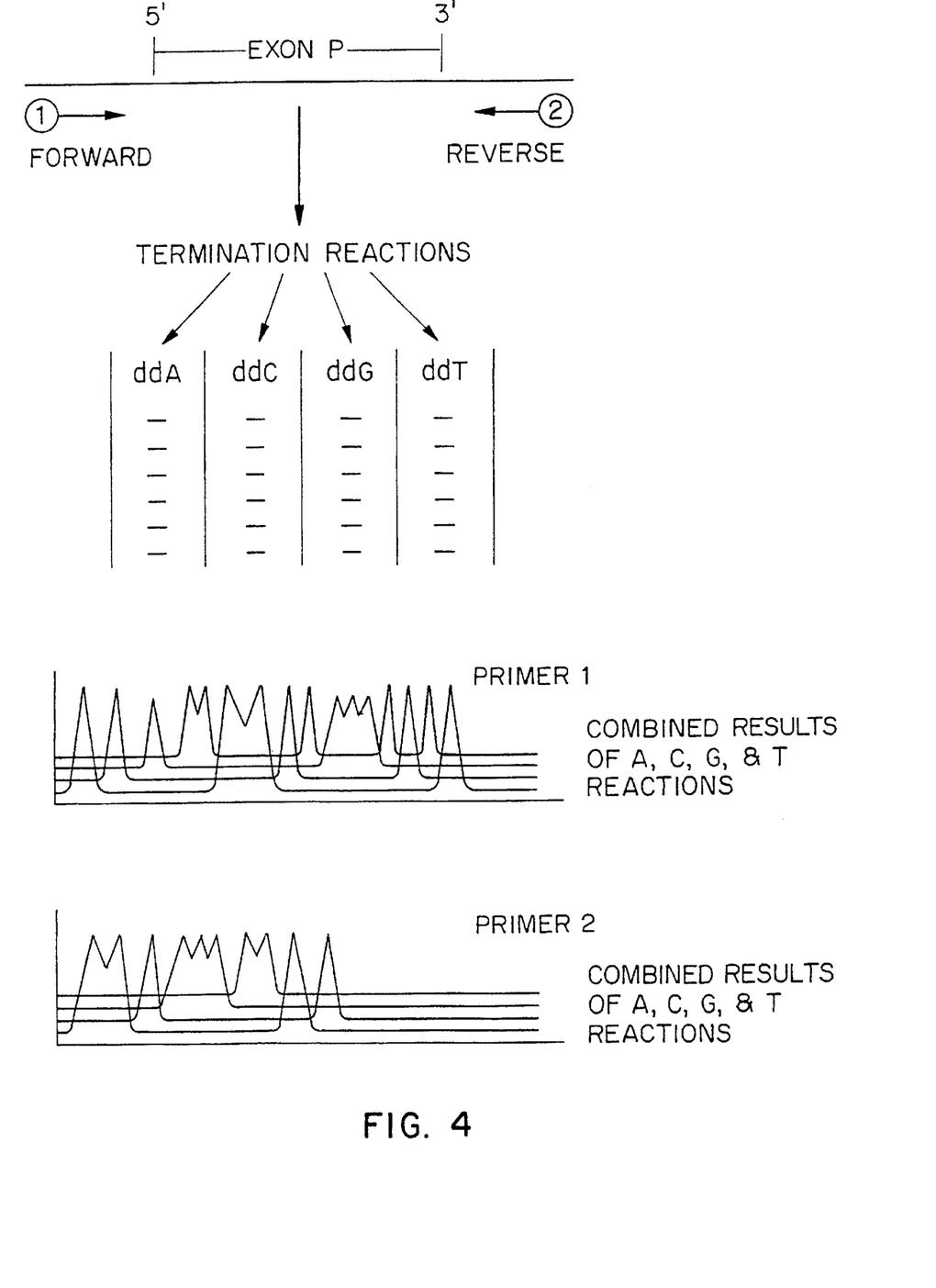
FIG. 4 illustrates a multi-dye embodiment of the invention.

The possibility of multi-dye detection leads to a wide range of applications for the invention which lead to improved accuracy in sequencing and to improved instrumental throughput. For example, FIG. 4 illustrates a method for obtaining both the forward and reverse sequences of a target nucleic acid sequence using two primers, each with a spectroscopically-distinguishable label. The natural abundance sample is mixed with forward and reverse primers, each with a distinguishable label (1 and 2). The reaction is performed with four termination reactions, one each for A, C, G and T. Each reaction is loaded into a single well of an automated sequencing instrument that detects and distinguishes at least the two labels employed. The results detected from label 1 are combined to give the forward sequence. The results detected from label 2 are combined to give the reverse sequence. The two sequences can be used to check each other and correct any ambiguities in base calling. In addition, the opposite sequence can be used to confirm sequence proximal to a primer which is found empirically to be difficult to determine on commercially available automated DNA sequencers.

Figure 5:
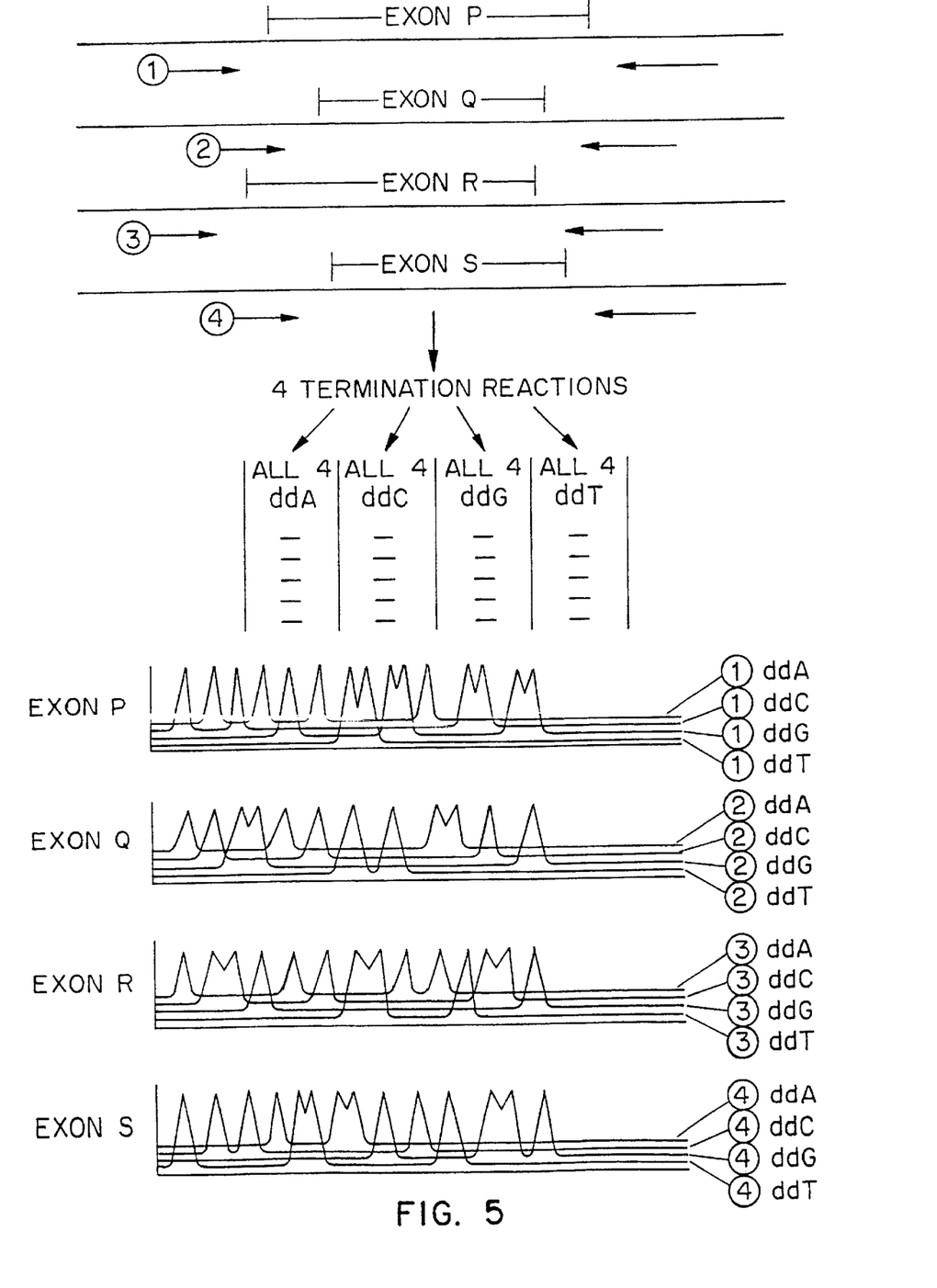
FIG. 5 illustrates a second multi-dye embodiment of the invention.

FIG. 5 demonstrates the use of multiple labels in a different format. In this case, assuming the instrument can distinguish between 4 labels, 4 genes or gene fragments in a single sample can be sequenced contemporaneously. 4 pairs of primers are added to patient sample genomic DNA. Each pair is specific for a different target, possibly 4 exons of the same gene of interest (P, Q, R and S). One member of each pair is conjugated to a detectable label (1, 2, 3, or 4) and each label is distinguishable from the others. This mixture is divided into four termination reaction tubes, one each for ddA, ddC, ddG and ddT, and thermally processed. Termination reaction products are loaded in one lane, thus employing the method as disclosed in U.S. patent application Ser. No. 08/634,284, assigned to the assignee of the instant invention and incorporated herein by reference. The results from each label are combined to give the sequence of the exon for which that primer is specific.

Figure 6A:
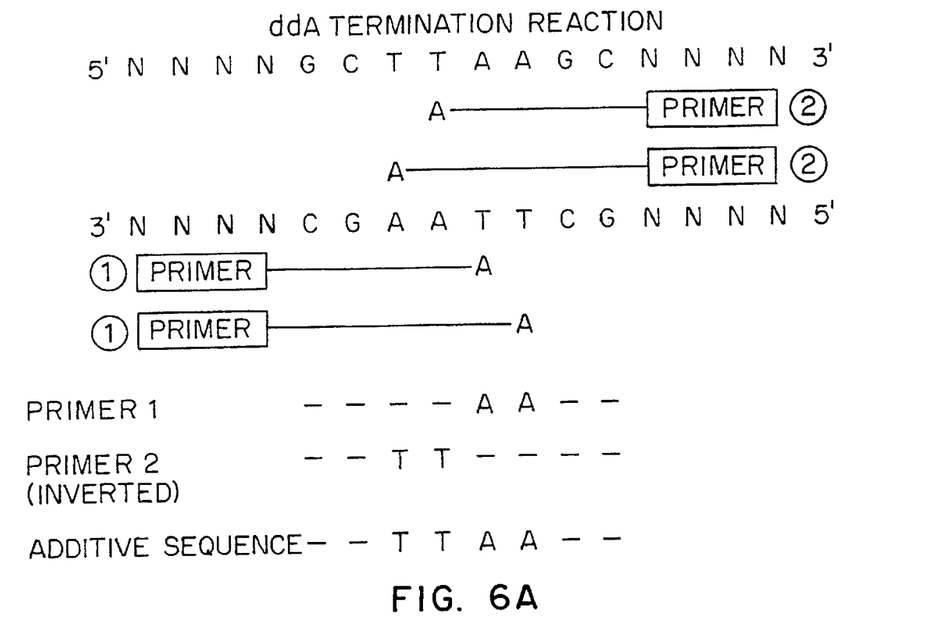
FIGS. 6A and 6B illustrate a third multi-dye embodiment of the invention.

Another embodiment takes advantage of the fact that a single ddA termination reaction identifies the A nucleotides from each strand, FIG. 6A, thus identifying the complementary base (in this case T) in the opposite strand. (i.e. the A termination sites on the opposite strand correspond to T nucleotide sites in the first strand). The complementary base can be located in the "missing" sites of the opposite strand. Note that sequence from the opposite strand must be inverted before it can be added in to the missing sites because it starts at the opposite end of the target gene and chain extension is in the opposite direction.

Figure 6B:
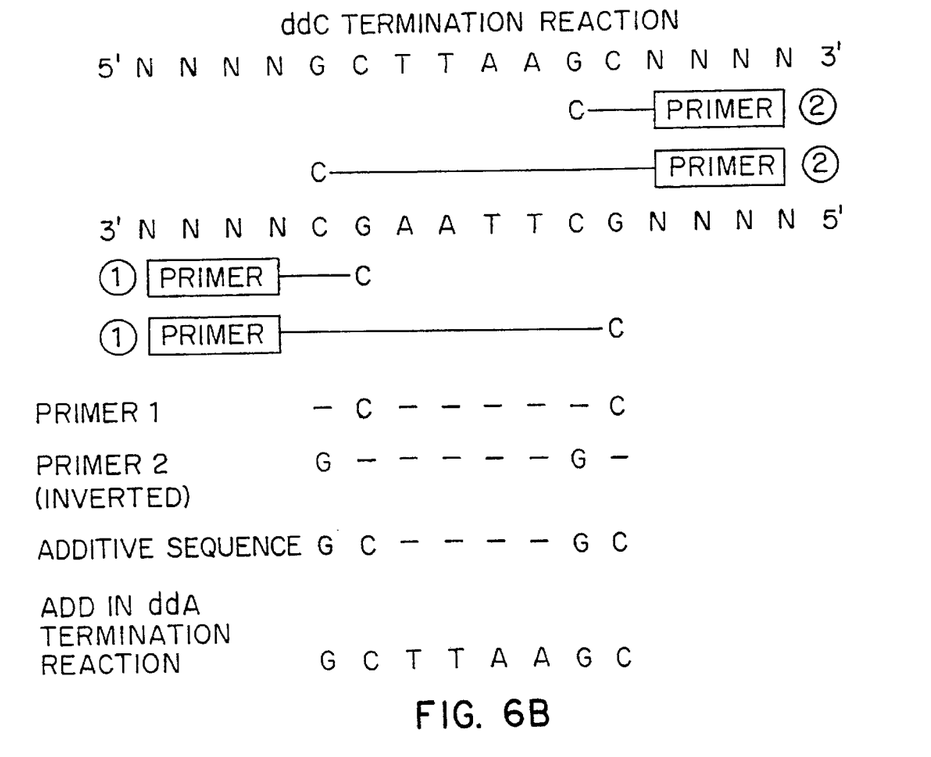

In FIG. 6B, a second termination reaction for ddC is added. This allows identification of C and its complement G in each strand. When these results are added to the first reaction, a full DNA sequence is obtained. Thus on the basis of 2 termination reactions employing one ddNTP chain terminator each, the full 4 lane sequence of a gene can be obtained.

The base-calling and compiling of sequences illustrated in FIGS. 6A and 6B can be facilitated using GeneObjects software (Visible Genetics Inc., Toronto) and employing techniques disclosed in U.S. patent application Ser. No. 08/497,202 U.S. Pat. No. 5,853,979 and Ser. No. 08/670,534, U.S. Pat. No. 5,916,747 incorporated herein by reference.

The method of the present invention is advantageously applied in many contexts including: (1) detection of mutations, particularly mutations of medical significance, in samples derived from a human patient, animal, plant or microorganism; (2) determination of HLA type ancillary to transplant procedures; (3) detection and identification of microorganisms, particularly pathogenic microorganisms, in a sample; and (4) in-situ sequencing reactions to produce sequencing fragments within a histological specimen which are then removed from a selected location on the tissue preparation and loaded onto a gel for sequence analysis. This latter approach is particularly useful for evaluation of archived samples in retrospective studies where the outcome of a disease condition is known, but the potentially causative mutation is not. This method can be used with labeled primers for single base sequencing (or multiple-base sequencing using multiple tissue samples).

The basic method of the invention can also be enhanced by various modifications without departing from the scope of the present invention. For example, improvements in reproducibility and sensitivity can be obtained by using a combination of an enzyme having a high affinity for incorporation of dideoxynucleotide triphosphates into the extending polymer, e.g., Thermo Sequenase™, and one having a low affinity for incorporation of dideoxynucleotide triphosphates into the extending polymer, e.g., Taq polymerase, under conditions where both enzymes are actively catalyzing template-dependent primer extension polymerization. As noted above, the high affinity enzyme produces almost entirely termination products, with very few of the polymers actually being extended to full length. On the other hand, the low affinity enzyme produces almost exclusively full length product, with relatively few termination products. Addition of the low affinity enzyme to the reaction mixture increases the sensitivity of the method by producing more full length material to be sequenced without increasing the processing time or adding processing steps. The increase in sensitivity can be controlled by varying the ratio of high affinity to low affinity enzyme present in the mixture.

It will be noted, however, that including of low affinity enzyme to produce full length product will also result in the formation of a very intense labeled full-length product peak. This peak may make analysis of the bases near the end of the sequence difficult. To obtain the benefits of increased sensitivity while making less full length product, it may be desirable to utilize a low affinity enzyme which is more thermolabile than Taq polymerase, such that the low affinity enzyme is essentially inactivated by the end of the first 15 to 25 cycles. This would allow the production of longer fragments early in the assay and the generation of more terminated fragments late in the assay.

The reaction mixture of the invention may also incorporate other additives which enhance the formation of sequencing fragments. For example, a product called TaqStart™ Antibody is a monoclonal antibody which binds to and blocks the activities of Taq polymerase. This antibody is added to PCR reactions using Taq polymerase to block enzyme activity during set-up at ambient temperature to prevent or reduce the formation of non-specific amplification products. TaqStart™ Antibody can be used in the present invention with Thermo Sequenase™ to reduce non-specific primer extension reactions.

The method of the invention may also be used in conjunction with Johnson & Johnson techniques known as "PCR IN A POUCH" which is described in U.S. Pat. No. 5,460,780 incorporated herein by reference.

While the preferred method for sequencing nucleic acid polymers in accordance with the invention involves the use of a single step procedure as described above, the invention also encompasses other uses of unconventional nucleotides during the preparation of sequencing fragments to provide a mechanism for reducing the risk of carry-over contamination in laboratories performing sequencing reactions through the addition of a preliminary degradation step prior to each sequencing procedure. Thus, in the broadest sense, the invention is a method for sequencing a nucleic acid polymer in a sample, in which the sample is combined with a reaction mixture containing an unconventional nucleotide, three conventional nucleotide bases, at least one type of one chain-terminating nucleotide triphosphate, a polymerase enzyme, and an enzyme for degrading polynucleotides containing the unconventional base. The sequencing reaction can be done as a single step from natural abundance DNA, as described above, or can be performed on a previously amplified (preferably using an unconventional nucleotide) sample. The sequencing fragments can be obtained using any known method, including cycle sequencing, CAS, bidirectional sequencing or conventional one extension sequencing.

The invention will now be further described with reference to the following non-limiting examples.

EXAMPLE 1

| DNA Amplification by PCR with dUTP and uracyl-n-glycosylase | |
|---|---|
| PCR Master Mix | |
| HK-UNG Dilution Buffer | 10 µl |
| HK-UNG | 1 µl |
| 10X PCR Buffer II | 55 µl |
| 25 mM MgCl2 | 66 µl |
| dNTP Mix | 66 µl |
| PCR Primers | 13 µl |
| Sterile water | 284 µl |
| AmpliTaq DNA Polymerase @ 5 U/µl | 2.8 µl |

Where

HK-UNG Dilution Buffer is 50 mM Tris-HCl (pH 7.5), 100 mM NaCl, 0.1 mM EDTA, 1 mM DTT, and 0.1% Triton X-100

HK-UNG is Thermolabile Uracyl-N-Glycosylase, Epicentre Technologies

10X PCR Buffer II: 100 mM Tris-HCl pH 8.3 @ 25° C.; 500 mM KCl dNTP Mix: 2.5 mM dATP, 2.5 mM dCTP, 2.5 mM dGTP, and 2.5 mM dUTP PCR Primers: 2.0 µM primer CT1590, 2.0 µM primer KL1-Cy5.5

Primer KL1-Cy5.55'-TCC GGA GCG AGT TAC GAA GA-3', labeled with Cy5.5

Primer CT15905'-ATG CCC GGG ATT GGT TGA TC-3', unlabeled

45 µl of the PCR Master Mix was put in a 200 µl thin-walled PCR tube.

5 µl of a recombinant plasmid (pUC8 containing the cryptic plasmid of Chlamydia trachomatis, serovar L1) at 400 copies/µl.

The tube was closed and put in the thermal cycler. The PCR was started with the following conditions
37° C. 15 min
75° C. 15 min
94° C. 5 min
37 cycles of the following
94° C. 30 sec
61° C. 30 sec
72° C. 45 sec
Then
72° C. 5 min
hold at 4° C.

Sequencing of the dUTP-containing amplicon by CLIP with dUTP
  CLIP Master Mix
  Sequencing Buffer 22 µl
  CLIP Primers 12 µl
  ThermoSequenase @ 32 U/µl 2.2 µl
  Sterile water 84.8 µl
  Where
  Sequencing BufferTris-HCl 260 mM pH 9.1 @ 25° C.; MgCl2 39 mM in ddH2O
  CLIP Primers: 2.0 µM primer CT1431F-Cy5.5, 2.0 µM primer CT1538R
  Primer CT1431F-Cy5.55'-GTG CAT AAA CTT CTG AGG AT-3', labeled with Cy5.5
  Primer CT1538R5'-GTA AAC GCT CCT CTG AAG TC-3', unlabeled
  11 µl of the CLIP Master Mix was added to a tube 2 µl of the dUTP-containing amplicon, created by the PCR reaction above, was added to the 11 µl of CLIP Master Mix, this is the Sample Master Mix 20 µl of sterile mineral oil was added to four 200 µl thin-walled PCR tubes 3 µl of the Sample Master Mix was added to each of the four tubes containing the mineral oil 3 µl of A-Sequencing Mix (750 µM dATP, 750 µM dCTP, 750 µM dGTP, 750 µM dUTP, 2.5 µM ddATP) was added to first of the four tubes 3 µl of C-Sequencing Mix (750 µM dATP, 750 µM dCTP, 750 µM dGTP, 750 µM dUTP, 2.5 µM ddCTP) was added to second of the four tubes 3 µl of G-Sequencing Mix (750 µM dATP, 750 µM dCTP, 750 µM dGTP, 750 µM dUTP, 2.5 µM ddGTP) was added to third of the four tubes 3 µl of T-Sequencing Mix (750 µM dATP, 750 µM dCTP, 750 µM dGTP, 750 µM dUTP, 2.5 µM ddTTP) was added to fourth of the four tubes The tubes were closed and put in the thermal cycler. The sequencing reactions were started with the following conditions
94° C. 5 min
37 cycles of the following
94° C. 10 sec 60° C. 15 sec
70° C. 45 sec
Then
70° C. 5 min
hold at 4° C.

The tubes were taken out of the thermal cycler, and 6 µl of loading dye was added to each tube (A, C, G, and T). 2 µl of each tubes containing the loading dye were migrated on a MICROGENE BLASTER sequencer at 50° C. for 20 minutes at a voltage of 1,300 volts.

After the run, the bases where determined.

EXAMPLE 2

| Sequencing an HIV dTTP-containing amplicon by CLIP with dUTP | |
|---|---|
| CLIP Master Mix | |
| Sequencing Buffer | 18.5 µl |
| HK-UNG | 1.0 µl |
| dTTP-Containing Amplicon | 5.0 µl |
| AmpliTAQ FS @ 15 U/µl | 4.0 µl |
| Sterile water | 69.5 µl |

Where

Sequencing Buffer: Tris-HCl 260 mM pH 8.3 @ 25° C.; MgCl2 32.5 mM in ddH2O dTTP-Containing Amplicon: a 1.3-kb amplicon at a concentration of 100 ng/µl, containing the sequence of the protease of HIV-1.

HK-UNG: Thermolabile Uracyl-N-Glycosylase, Epicentre Technologies

7 µl of A-Termination Mix (640 mM dATP, 640 mM dCTP, 640 mM dGTP, 640 mM dUTP, 1 µM ddATP, 163 mM primer PR170F-Cy5.5, 163 nM primer PR170F-A-Cy5.5, 131 nM primer PR543R-Cy5.0, 200 nM primer PR543R) was added to a 200 µl thin-walled PCR tube.

7 µl of C-Termination Mix (640 mM dATP, 640 mM dCTP, 640 mM dGTP, 640 mM dUTP, 2 µM ddCTP, 163 mM primer PR170F-Cy5.5, 163 nM primer PR170F-A-Cy5.5, 131 nM primer PR543R-Cy5.0, 200 nM primer PR543R) was added to a 200 µl thin-walled PCR tube.

7 µl of G-Termination Mix (640 mM dATP, 640 mM dCTP, 640 mM dGTP, 640 mM dUTP, 2 µM ddGTP, 163 mM primer PR170F-Cy5.5, 163 nM primer PR170F-A-Cy5.5, 131 nM primer PR543R-Cy5.0, 200 nM primer PR543R) was added to a 200 µl thin-walled PCR tube.

7 µl of T-Termination Mix (640 mM dATP, 640 mM dCTP, 640 mM dGTP, 640 mM dUTP, 2 µM ddTTP, 163 mM primer PR170F-Cy5.5, 163 nM primer PR170F-A-Cy5.5, 131 nM primer PR543R-Cy5.0, 200 nM primer PR543R) was added to a 200 µl thin-walled PCR tube.

Where

Primer PR170F-Cy5.5: 5'-GAG CCR ATA GAC AAG GAA YTR TAT-3', labeled with Cy5.5

Primer PR170F-A-Cy5.5: 5'-GAG MCG ATA GAC AAG GRV CTG TAT-3', labeled with Cy5.5

Primer PR543R-Cy5.5: 5'-ACT TTT GGG CCA TCC ATT CCT-3', labeled with Cy5.0

Primer PR543R-Cy5.5: 5'-ACT TTT GGG CCA TCC ATT CCT-3', unlabeled

5 µl of the CLIP Master Mix was added to each of the four tubes containing the Termination Mixes.

The tubes were closed and put in the thermal cycler. The sequencing reactions were started with the following conditions 37° C. 15 min
75° C. 15 min
94° C. 5 min
30 cycles of the following
94° C. 20 sec
56° C. 20 sec
70° C. 90 sec
Then
70° C. 5 min
hold at 4° C.

The tubes were taken out of the thermal cycler, and 12 µl of loading dye was added to each tube (A, C, G, and T). 2 µl of each tubes containing the loading dye were migrated on a Clipper (two dye automated sequencer) at 54° C. for 35 minutes at a voltage of 1,400 volts. After the run, the bases where determined on both orientation (forward and reverse).

EXAMPLE 3

| Cycle Sequencing Sequencing M13 with dUTP | |
|---|---|
| Sequencing Master Mix | |
| HK-UNG diluted 1/10 | 1.0 µl |
| Sequencing Buffer | 2.0 µl |
| Primer at 3 µM | 1.0 µl |
| M13 ssDNA | 1.0 µl |
| ThermoSequenase @ 3.2 U/µl | 2.5 µl |
| Sterile water | 5.5 µl |

Where

Sequencing Buffer: Tris-HCl 260 mM pH 8.3 @ 25° C.; MgCl2 39 mM in ddH2 O

PrimerM13 Universal-Cy5.5: 5'-GTA AAA CGA CGG CCA GT-3', labeled with Cy5.5

M13 ssDNA: single stranded DNA (M13) at 200 ng/µl

HK-UNG: Thermolabile Uracyl-N-Glycosylase, Epicentre Technologies

Aliquot 3 µl of A-Termination Mix (750 µM dATP, 750 µM dCTP, 750 µM Dgtp, 750 µM dUTP, 2.5 µM ddATP) in a 200 µl thin-walled PCR tube.

Aliquot 3 µl of C-Termination Mix (750 µM dATP, 750 µM dCTP, 750 µM dGTP, 750 µM dUTP, 2.5 µM ddCTP) in a 200 µl thin-walled PCR tube.

Aliquot 3 µl of G-Termination Mix (750 µM dATP, 750 µM dCTP, 750 µM dGTP, 750 µM dUTP, 2.5 µM ddGTP) in a 200 µl thin-walled PCR tube.

Aliquot 3 µl of T-Termination Mix (750 µM dATP, 750 µM dCTP, 750 µM dGTP, 750 µM dUTP, 2.5 µM ddTTP) in a 200 µl thin-walled PCR tube.

Aliquot 3 µl of the Sequencing Master Mix in each of the termination tubes. Close the tubes and put them in the thermal cylcer. Start the sequencing reaction with the following conditions 37° C. 15 min
75° C. 15 min
94° C. 2 min
35 cycles of the following
94° C. 40 sec
50° C. 20 sec
72° C. 60 sec
Then
72° C. 2 min
hold at 4° C.

Take the tubes out of the thermal cycler, and add 6 µl of loading dye to each tube (A, C, G, and T). Migrate 2 µl of each tubes containing the loading dye a MICROGENE BLASTER sequencer at 54° C. for 35 minutes at a voltage of 1,400 volts. After the run, analyse the data to determine the sequence.

What is claimed is:

1. A method for determining the position of at least one selected species of nucleotide within a region of interest in a target nucleic acid polymer in a sample comprising the steps of combining the sample with a reaction mixture to synthesize chain-extension products indicative of the positions of the selected species of nucleotide within the region of interest and evaluating the products thus produced, wherein the reaction mixture which is combined with the sample comprises an unconventional nucleotide and a first enzyme said first enzyme being effective to degrade polynucleotides incorporating the unconventional nucleotide.

2. The method according to claim 1, wherein target and non-target nucleic acid polymers are present in the sample in substantially natural relative abundance.

3. The method according to claim 2, wherein the reaction mixture further comprises a thermally-stable polymerase enzyme which incorporates dideoxynucleotides into an extending nucleic acid polymer at a rate which is no less than 0.4 times the rate of incorporation of deoxynucleotides.

4. The method according to claim 1, wherein the reaction mixture further comprises at least two oligonucleotide primers which, when hybridized to the target DNA, are oriented to allow chain extension towards each other across the region of interest.

5. A method according to claim 1, comprising the steps of:
   (a) combining the sample in the reaction mixture with first and second primers, a nucleotide triphosphate feedstock mixture, a chain-terminating nucleotide triphosphate and a thermally stable polymerase enzyme, said first and second primers binding to the sense and antisense strands, respectively, of the target nucleic acid polymer at locations flanking the selected region;
   (b) incubating the reaction mixture for a period of time sufficient to permit degradation of any nucleic acid polymers including the unconventional nucleotide by the first enzyme;
   (c) exposing the reaction mixture after the incubation step to a plurality of temperature cycles each of which includes at least a high temperature denaturation phase and a lower temperature extension phase, thereby producing a plurality of terminated fragments; and
   (c) evaluating terminated fragments produced during the additional cycles to determine the positions of the nucleic acid corresponding to the chain-terminating nucleotide triphosphate within the selected region, characterized in that the sample contains target nucleic acid polymer and non-target nucleic acid polymer in natural abundance and that the polymerase is one which incorporates dideoxynucleotides into an extending nucleic acid polymer at a rate which is no less than 0.4 times the rate of incorporation of deoxynucleotides.

6. The method according to claim 5, wherein target and non-target nucleic acid polymers are present in the sample in substantially natural relative abundance.

7. The method of claim 6, wherein the mole ratio of the dideoxynucleotide triphosphate to the corresponding deoxynucleotide triphosphate in the reaction mixture is from 1:50 to 1:1000.

8. The method of claim 6, wherein the mole ratio of the dideoxynucleotide triphosphate to the corresponding deoxynucleotide triphosphate is from 1:100 to 1:300.

9. The method of claim 1, wherein at least one of the primers is labeled with a fluorescent label.

10. The method of claim 9, wherein the primers are each labeled with a different fluorescent label.

11. The method of claim 1, wherein the enzyme is a glycosylase.

12. The method according to claim 1, wherein the unconventional nucleotide is dUTP.

13. The method of claim 12, wherein the enzyme is a glycosylase.

14. The method according to claim 1, wherein the reaction mixture further comprises a second polymerase enzyme having a low affinity for incorporation of dideoxynucleotide triphosphates compared to deoxynucleotide triphosphates.

15. The method according to claim 14, wherein the second polymerase is Taq polymerase.

* * * * *